(12) United States Patent
Ichikawa et al.

(10) Patent No.: US 8,545,473 B2
(45) Date of Patent: Oct. 1, 2013

(54) WEARING ARTICLE WITH CORRUGATED FASTENERS

(75) Inventors: Makoto Ichikawa, Kagawa (JP); Naoto Ohashi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 502 days.

(21) Appl. No.: 12/739,498

(22) PCT Filed: Aug. 14, 2008

(86) PCT No.: PCT/JP2008/064594
§ 371 (c)(1),
(2), (4) Date: Aug. 19, 2010

(87) PCT Pub. No.: WO2009/054178
PCT Pub. Date: Apr. 30, 2009

(65) Prior Publication Data
US 2010/0312218 A1    Dec. 9, 2010

(30) Foreign Application Priority Data
Oct. 25, 2007    (JP) ................................. 2007-278176

(51) Int. Cl.
*A61F 13/49* (2006.01)
*A61F 13/56* (2006.01)
*A61F 13/58* (2006.01)
*A61F 13/62* (2006.01)

(52) U.S. Cl.
USPC ...... 604/386; 604/385.24; 604/389; 604/391; 604/394

(58) Field of Classification Search
USPC ................. 604/386, 387, 389–391, 393, 394; 24/442, 444–449
See application file for complete search history.

(56) References Cited

U.S. PATENT DOCUMENTS 5,032,122 A * 7/1991 Noel et al. .................... 604/391
5,624,427 A * 4/1997 Bergman et al. .............. 604/391

(Continued)

FOREIGN PATENT DOCUMENTS

| JP | 5-93427 | 12/1993 |
| JP | 2002-532147 | 10/2002 |

(Continued)

OTHER PUBLICATIONS

International Search Report from corresponding PCT application No. PCT/JP2008/064594, dated Nov. 18, 2008, 4 pages.

*Primary Examiner* — Jackie Ho
*Assistant Examiner* — Kathryn E Ditmer
(74) *Attorney, Agent, or Firm* — Brinks Hofer Gilson & Lione (57) ABSTRACT

A wearing article having a front waist region provided along a pair of opposite side edges with first fastening members, and a rear waist region provided along a pair of opposite side edges with second fastening members adapted to be engaged with the associated first fastening members. Each of the second fastening members is formed with an uneven structure having a plurality of crests extending in a transverse direction and spaced one from another in a longitudinal direction. A degree of engaging force between the uneven structure and the first fastening member is extremely weak and the uneven structure can be easily disengaged from the first fastening member. The uneven structure may be unfolded in the longitudinal direction and put in close contact with the first fastening member to achieve firm engagement over an area as large as possible between the flattened uneven structure and the first fastening member.

3 Claims, 6 Drawing Sheets

(56) References Cited

U.S. PATENT DOCUMENTS

| | | | |
|---|---|---|---|
| 2004/0261230 A1* | 12/2004 | Neeb et al. | 24/451 |
| 2005/0080394 A1 | 4/2005 | Otsubo et al. | |
| 2005/0132543 A1* | 6/2005 | Lindsay et al. | 24/442 |
| 2008/0009820 A1* | 1/2008 | Kenmochi et al. | 604/389 |

FOREIGN PATENT DOCUMENTS

| | | |
|---|---|---|
| JP | 2005-95574 | 4/2005 |
| JP | 2005-095648 | 4/2005 |
| WO | WO 00/35398 | 6/2000 |

* cited by examiner

WEARING ARTICLE WITH CORRUGATED FASTENERS

RELATED APPLICATION

This application is a 35 U.S.C. §371 national phase filing of International Patent Application No. PCT/JP2008/064594, filed Aug. 14, 2008, through which and to which priority is claimed under 35 U.S.C. §119 to Japanese Patent Application No. 2007-278176, filed Oct. 25, 2007.

TECHNICAL FIELD

The present invention relates to wearing articles and particularly to wearing articles such as disposable diapers, toilet-training pants, incontinent briefs, or diaper covers and the like.

RELATED ART

Disposable diapers having front and rear waist regions detachably fastened together along transversely opposite side edges of diapers is known, for example, from the disclosure of JP 2002-532147W. According to the disclosure of JP 2002-532147W, a diaper comprises a liquid-absorbent chassis which comprises, in turn, front and rear waist regions, a crotch region and the inner side facing the wearer's skin and the outer side facing the wearer's garment, and hook elements and loop elements provided along the side edges of the front and rear waist regions. Specifically, the loop elements are provided on the outer side facing the garment of the front waist region along its transversely opposite side edges and the hook elements are provided on the inner side facing the wearer's skin of the rear waist region along its transversely opposite side edges so that these loop and hook elements may be engaged together to make the diaper in a pant-shape.
PATENT DOCUMENT 1: JP 2002-532147W

DISCLOSURE OF THE INVENTION

Problem to be Solved by the Invention

According to the disclosure, the hook and loop elements extend in a longitudinal direction along the transversely opposite side edges of the front and rear waist regions, respectively. Lengths of the hook and loop elements are dimensioned to be substantially equal to lengths of the respective side edges to enlarge the area over which these elements are engaged one with another and thereby to enhance the fastening effect. Operation of engaging the hook and loop one with another is carried out, for example, as will be described. Such operation is started by engaging the longitudinally upper end of the hook element with associated upper end of the loop element for positioning followed by engaging the remaining portions of the respective elements with one another. However, the longitudinally lower portions of the respective elements should be unintentionally engaged with one another in the course of positioning the upper ends, resulting in a misaligned engagement. To remedy this, the unintentionally engaged portions must be disengaged from each other and it must be tried to engage again these portions with each other so as to assure the proper positioning, i.e., the proper alignment. In this regard, the fastening means adopted by the disposable diaper cited above has left unsolved a problem such that time and labor should be taken for handling of the fastening means. This problem has been significant particularly in the adult diaper of large size.

In view of the problem as has been discussed above, the present invention provides a wearing article improved so that the front waist region and the rear waist region can be easily and normally engaged with each other.

Measure to Solve the Problem

According to the present invention, there is provided a wearing article comprising a liquid-absorbent chassis having a longitudinal direction, a transverse direction, an inner side facing the wearer's skin, an outer side facing the wearer's garment, a front waist region, a rear waist region and a crotch region extending between the front and rear waist region, and fastening means adapted to detachably fasten the front and rear waist regions to each other along respective pairs of side edges thereof opposed in the transverse direction and extending in the longitudinal direction.

The present invention is characterized in that the fastening means comprise first fastening members attached to the side edges of the front waist region so as to extend in the longitudinal direction and second fastening members attached to the side edges of the rear waist region and extending in the longitudinal direction so as to be detachably engaged with the first fastening members, and the first fastening members or the second fastening members is formed with uneven regions elastically extensible in the longitudinal direction each adapted, in its contracted state, to form an uneven structure having a plurality of crests extending in the transverse direction and spaced one from another in the longitudinal direction.

According to one preferred embodiment, the uneven structure is formed by the elastic members which are attached under tension in the longitudinal direction to said first fastening members or the second fastening members.

According to another preferred embodiment, said first fastening members or the second fastening members provided with the uneven structures are made of thermoplastic resin and formed by thermally deforming the first fastening members or the second fastening members.

According to still another preferred embodiment, the crests are collapsed as a result of thermal deforming process so that the first fastening members and the second fastening members can no more be engaged one with another.

According to yet another preferred embodiment, the first fastening member or the second fastening member provided with the uneven structures has a flat region at least one of upper and lower ends opposed to each other in the longitudinal direction, wherein the flat region is formed with none of the crests.

According to further another preferred embodiment, one of the first fastening member and the second fastening member includes a plurality of hook elements and the other includes a plurality of loop elements adapted to be detachably engaged with the hook elements.

Effect of the Invention

The first fastening member or the second fastening member is formed with the uneven structure having a plurality of crests extending in the transverse direction and spaced one from another in the longitudinal direction so that the first fastening member and the second fastening member may be unintentionally engaged with each other along these crests so far as the uneven structure is in contracted and folded state. However, such an engagement is extremely weak and the first and second fastening members can be easily disengaged from each other. After the uneven structure has been unfolded and flattened, the first and second fastening members may be put in engagement with each other to ensure firm and accurate engagement over an area as large as possible.

The crests may be subjected to the heat press processing to make such unintentional engagement impossible and thereby to make it easy to restart the operation of engagement.

The first fastening member or the second fastening member provided with the uneven structure is formed at its upper or lower end with the flat region having none of the crests. With this unique arrangement, the flat region may be first put in engagement with the associated fastening member and then the uneven structure may be unfolded and flattened to achieve the engagement between the first and second fastening members over the entire area.

IDENTIFICATION OF REFERENCE NUMERALS USED IN THE DRAWINGS 1 diaper
2 liquid-absorbent chassis
3 fastening means
4 inner side
5 outer side
8 front waist region
9 rear waist region
10 crotch region
11 side edge
12 side edge
13 first fastening member
14 second fastening member
15 elastic member
16 uneven region
17 crest
18 upper end
19 lower end
20 flat region
21 flat region

DESCRIPTION OF THE BEST MODE FOR WORKING OF THE INVENTION

First Embodiment

Figure 1:
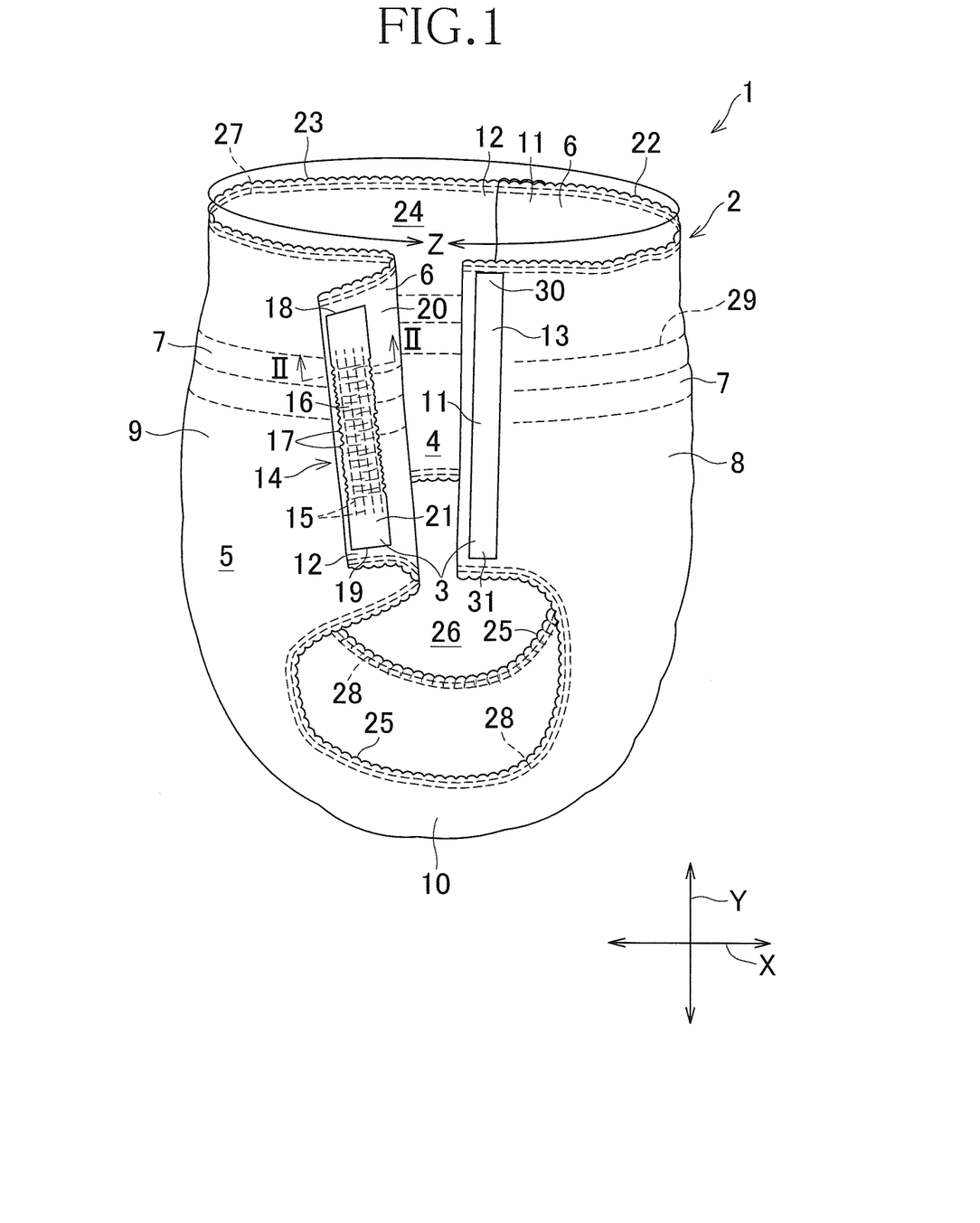
FIG. 1 is a perspective view showing a first embodiment of a diaper according to the first aspect of the present invention.

FIG. 1 through 5 illustrate a first embodiment according to the present invention and a diaper for adult will be exemplarily described hereunder with reference to FIG. 1 through 5. As shown in FIG. 1, a diaper 1 comprises a liquid-absorbent chassis 2 and fastening means 3. The liquid-absorbent chassis 2 has a longitudinal direction Y, a transverse direction X, a waist-circumferential direction Z, an inner side 4 facing the wearer's skin and an outer side 5 facing the wearer's garment. With regard to components, the liquid-absorbent chassis 2 comprises an inner sheet 6 defining the inner side 4 facing the wearer's skin, an outer sheet 7 defining the outer side facing the wearer's garment and a liquid-absorbent core (not shown) interposed between these inner and outer sheets 6, 7. Such liquid-absorbent chassis 2 configurationally comprises a front waist region 8, a rear waist region 9 and a crotch region 10 extending between the front and rear waist regions 8, 9.

The front waist region 8 has side edges 11 opposed in the transverse direction X and extending in the longitudinal direction Y and the rear waist region 9 has side edges 12 opposed in the transverse direction X and extending in the longitudinal direction Y. The outer sheet 7 is provided along the side edges 11 of the front waist region with first fastening members 13 each including hook elements attached thereto by use of adhesive or welding technique.

The inner sheet 6 is provided along the side edges 12 of the rear waist region with second fastening members 14 each including loop elements attached thereto by use of adhesive or welding technique so that the second fastening members 14 may be detachably engaged with the associated first fastening members 13. Between the inner sheet 6 and the respective second fastening members 14, elastic members 15 extending in the longitudinal direction Y are attached to them under tension. The first fastening members 13 respectively have substantially the same dimensions as the side edges 11 of the front waist region as measured in the longitudinal direction Y. While FIG. 1 shows one of the second fastening members 14 and the associated side edge 12 of the rear waist region both contracted under the effect of the associated elastic members 15, these second fastening member 14 and the side edge 12 have substantially the same dimension as measured in the longitudinal direction Y in a stretched state thereof. This is true also for a dimensional relationship between the first fastening members 13 and the second fastening members 14.

Figure 2:
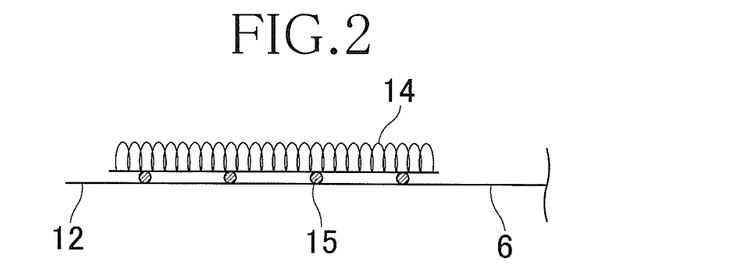
FIG. 2 is a sectional view taken along the line II-II in FIG. 1.

FIG. 2 is a sectional view taken along the line II-II in FIG. 1. As will be apparent from FIG. 2, the elastic member 15 comprises four rubber strings arranged at regular intervals of about 5 mm in the transverse direction X. While the rubber strings are made of synthetic rubber of polyurethane in the illustrated embodiment, the present invention is not limited to this particular type of the elastic member 15 and the other types of the elastic member 15 may be adopted without departing from the scope of the invention. The number of the elastic elements constituting the elastic member 15 is not limited to four and may be appropriately selected taking account of particular materials used for the elastic member 15.

As shown in FIG. 1, the elastic member 15 is attached under tension to the associated second fastening member 14 and, upon contraction, causes this second fastening member 14 to actualize its uneven region 16 to form uneven-structure. Specifically, the elastic member 15 is attached to the second fastening member 14 substantially in a middle portion thereof as viewed in the longitudinal direction Y. In the uneven region 16, a plurality of gathers are formed under a contractile force of the elastic member 15 and these gathers define a plurality of crests 17 which are convex toward the first fastening member 13. The crests 17 respectively extend in the transverse direction X and spaced one from another in the longitudinal direction Y. While the second fastening members 14 are attached to the side edges 12 of the rear waist region of the liquid-absorbent chassis 2, the liquid-absorbent chassis 2 also is contracted as the uneven region 10 contract since the liquid-absorbent chassis 2 is formed from a soft touch nonwoven fabric.

A contractile force of the elastic member 15 is exerted neither on the upper end 18 nor on the lower end 19 of the second fastening member 14. Specifically, these upper and lower ends 18, 19 define flat regions 20, 21 having none of the crests 17. While each of these flat regions 20, 21 is illustrated to have a dimension of about 30 mm as measured in the longitudinal direction Y, this dimension may be set to a range of about 10 mm to 50 mm. This is for the reason that, if this dimension is smaller than about 10 mm, the engagement in the course of positioning as will be described later will be too weak to keep the engagement stable and, if this dimension is larger than about 50 mm, these flat regions 20, 21 may twist and get wrinkled in the course of positioning. The dimension of the second fastening member 14 in the longitudinal direction Y in the state free from the contractile force of the elastic member 15 and the dimension of the first fastening member 13 in the longitudinal direction Y are respectively set to about 130 mm. Dimensions of these first and second fastening members 13, 14 in the transverse direction X are respectively set to about 20 mm.

These first and second fastening members 13, 14 may be engaged together to join the front waist region 8 with the rear waist region 9 and thereby to obtain the diaper 1 of pant-type as shown in FIG. 1. In the diaper 1 of pant-type, a waist-opening 24 is defined by respective upper edges 22, 23 of the front and rear waist regions 8, 9, i.e., the edges cooperating with each other to define a peripheral edge of the waist-opening 24 and a pair of leg-openings 26 defined by transversely opposite side edges 25, 25 of the crotch region 10, i.e., the edges adapted to define peripheral edges of the respective leg-openings 26. The front and rear halves 22, 23 of the waist-opening's peripheral edge are provided with waist elastic members 28 attached thereto under tension so as to extend along these halves of 22, 23 of the waist-opening's peripheral edge. The leg-openings' peripheral edges 25, 25 are provided with leg elastic members 28, 28 attached thereto under tension so as to extend along these peripheral edges 25, 25, respectively. Both the waist elastic members 27 and the leg elastic members 28 comprise a plurality of rubber strings so that a desired fit of the front and rear halves 22, 23 of the waist-opening's peripheral edge and of the respective leg-openings' peripheral edges 25, 25 may be assured by a contractile force of these rubber strings.

The front and rear waist regions 8, 9 are provided at substantially middle levels as viewed in the longitudinal direction Y with auxiliary elastic members 29, 29 attached thereto under tension to provide a good fit of the diaper 1 to the wearer's body. The auxiliary elastic member 29 extends around the wearer's waist in a circumferential direction Z and comprises a plurality of rubber strings arranged to be spaced one from another in the longitudinal direction Y so that a contractile force of these rubber strings may ensure the front and rear waist regions to fit to the wearer's body at the respective middle levels of the front and rear waist regions 8, 9 thereof.

For the waist elastic member 27, the leg elastic member 28 and the auxiliary elastic member 29, natural rubber or synthetic rubber such as that made of polyurethane may be used and it is possible to implement these elastic members in the form of an elasticized fibrous nonwoven fabric or elasticized plastic sheet instead of the rubber strings.

Figure 3:
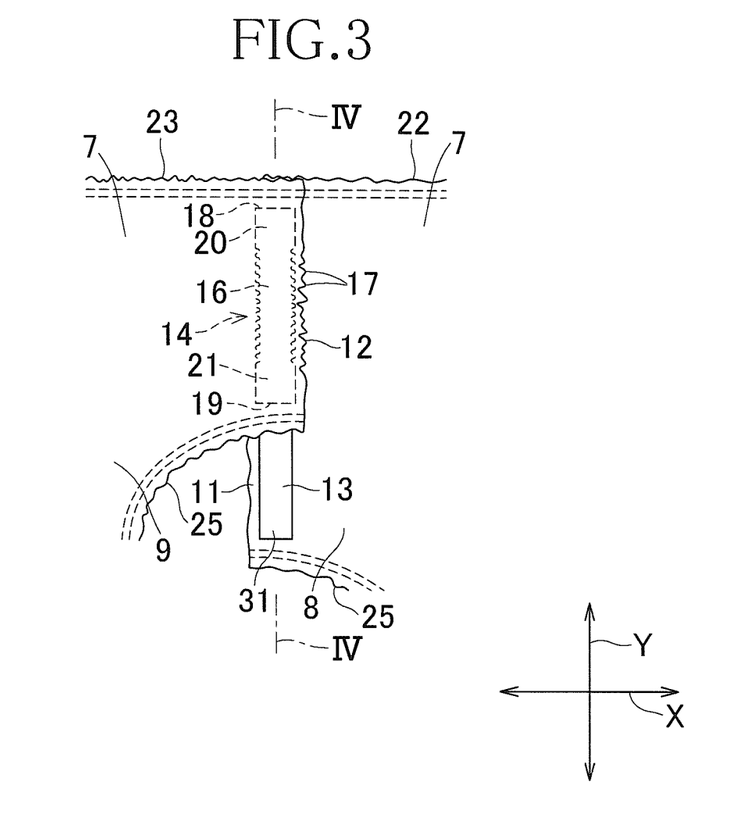
FIG. 3 is a diagram partially illustrating front and the rear waist regions as partially engaged together.

Now a manner of engagement between the first fastening member 13 and the second fastening member 14 will be described with reference to FIG. 3 through 5. FIG. 3 is a diagram illustrating the first fastening member 13 and the second fastening member 14 partially fastened together and FIG. 4 is a schematic sectional view taken along the line IV-IV in FIG. 3.

Figure 4:
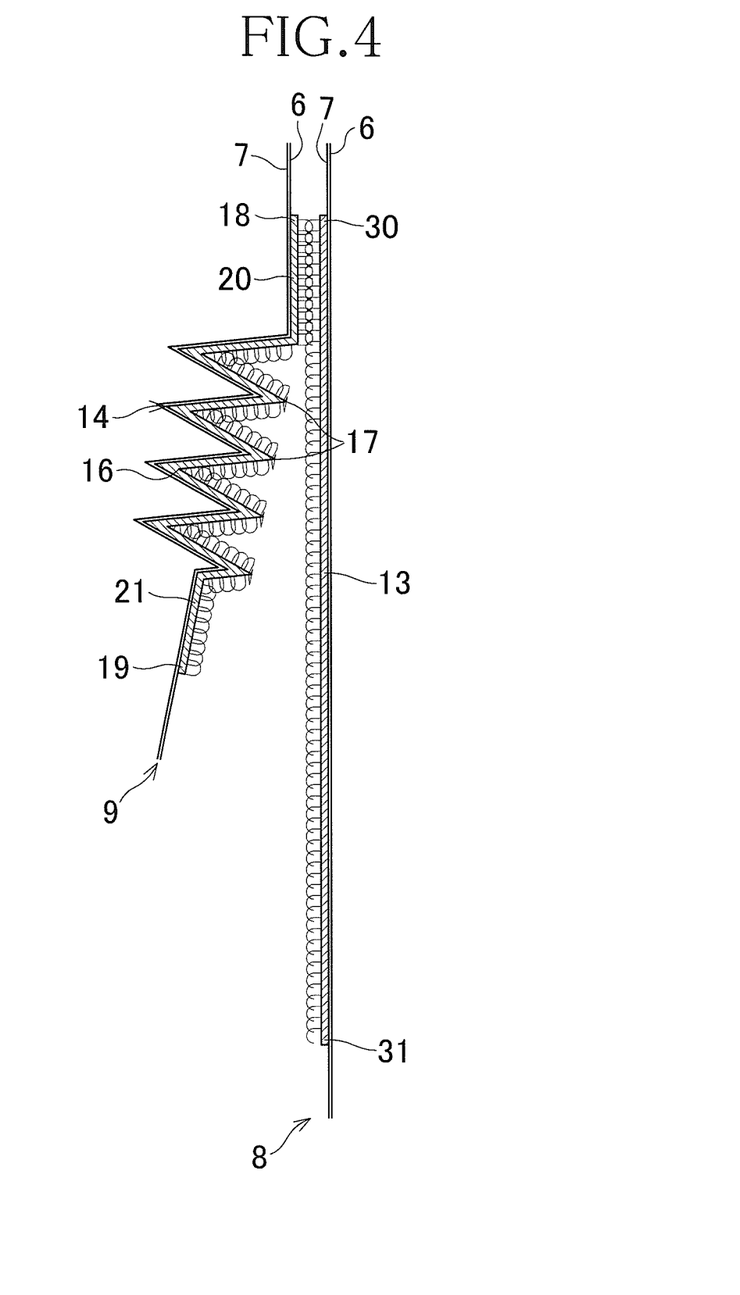
FIG. 4 is a schematic sectional view taken along the line IV-IV in FIG. 3.
Figure 5:
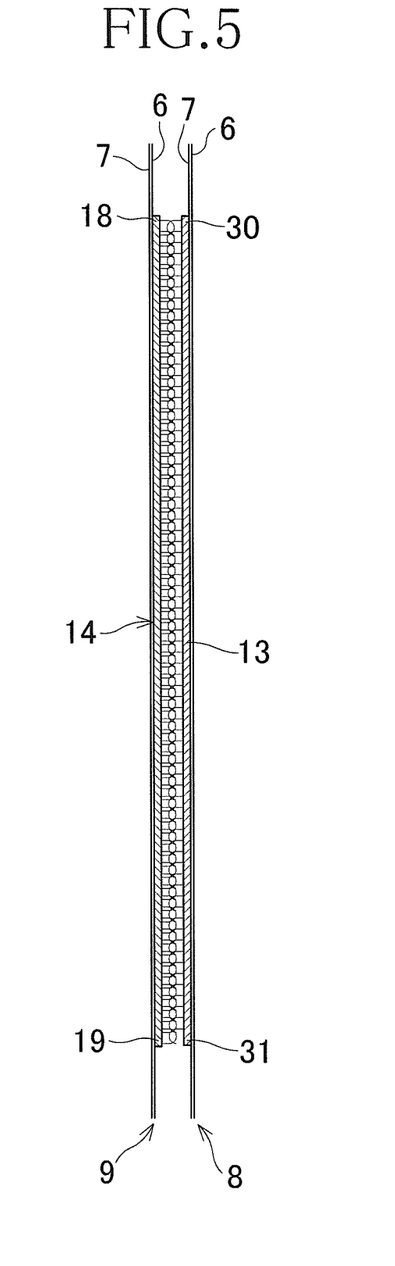
FIG. 5 is a diagram schematically illustrating the front and rear waist regions as partially engaged together.

As will be obvious from FIGS. 3 and 4, the upper end 18, i.e., the flat region 20 of the second fastening member 14 is placed on the upper end 30 of the first fastening member 13 and engaged therewith. The first fastening member 13 is flat over its entire length in the longitudinal direction Y and the flat region 20 of the second fastening member 14 is placed on the upper end 30 of the first fastening member 13. In consequence, the flat region 20 of the second fastening member 14 can be engaged with the upper end of the first fastening member 13 can be reliably engaged to each other over the entire areas of the respective upper ends 20, 30 and thereby the first fastening member 13 and the second fastening member 14 can be relatively positioned in alignment with each other.

As will be supposed from FIG. 4, the respective remaining regions of the first fastening member 13 and the second fastening member 14 should unintentionally come in contact and even in engagement with each other in the course of engaging the upper end 30 of the first fastening member 13 with the flat region 20 of the second fastening member 14. However, the second fastening member 14 is provided in its middle with the uneven region 16 having a plurality of the crests 17 and the unintentional contact and engagement as has been described above may occur only along the crests 17. In other words, the area in which such an unintentional engagement may occur is can be sufficiently limited to facilitate the unintentionally engaged portions of the first and second fastening members 13, 14 to be disengaged from each other. For example, the second fastening member 14 may be held by the wearer's fingers in the vicinity of the lower end 19 thereof and merely pulled in a direction of receding from the first fastening member 13 (i.e., leftward as viewed in FIG. 4) to disengage the uneven region 16 from the first fastening member 13 without any annoying handling. In the course of disengaging the uneven region 16 from the first fastening member 13 with the lower end 19 of the second fastening member 14 held by the fingers, the flat region 20 of the second fastening member 14 also should not be disengaged from the upper end 30 of the first fastening member 13. This is for the reason that the flat region 20 of the second fastening member 14 and the upper end 30 of the first fastening member 13 are kept firmly engaged with each other over the respective entire areas thereof.

The uneven region 16 of the second fastening member 14 peeled off from the first fastening member 13 is now properly positioned and engaged with the first fastening member 13. For example, the flat region 21 defined in the vicinity of the lower end 19 is held by the fingers and pulled downward in the longitudinal direction Y (downward as viewed in FIG. 4). The flat region 20 of the second fastening member 14 defined in the vicinity of its upper end 18 is firmly engaged with the first fastening member 13 so that the uneven structure formed in the uneven region 16 may be unfolded and flattened as the flat region 21 in the vicinity of the lower end 19 is pulled downward, as illustrated in FIG. 5. Consequently, the second fastening member 14 as a whole is extended downward in the longitudinal direction Y. With the uneven region 16 extended in this manner, the flat region 21 defined in the vicinity of the lower end 19 is engaged with the lower end 31 of the first fastening member 13 and then the extended uneven region 16 is enforced in engagement with the first fastening member 13. In this way, the uneven region 16 substantially flattened enables the second fastening member 14 to be engaged in its entire area with the first fastening member 13 and thereby enables the engaging force to be enhanced.

As has been described above, the uneven region 16 provided in the second fastening member 14 advantageously ensures that the portions of the second fastening member 14 and the first fastening member 13 having been unintentionally engaged with each other can be easily disengaged from each other to do the handling of engagement again normally. In addition, the presence of the uneven region 16 allows the first and second fastening members 13, 14 to be firmly and normally engaged with each other over the entire areas thereof.

The second fastening members 14 are attached to the rear waist regions 9 along the side edges thereof so that the rear waist region 9 may be placed on the front waist region 8 from outside to couple these two waist regions 8, 9. The uneven regions 16 of the respective second fastening members 14 present on the side edges placed on the associated side edges from outside facilitate these regions 16 to be unfolded and flattened. If the front waist region 8 is placed on the rear waist region 9 from outside, it is also possible to provide the uneven regions on the first fastening members 13.

While the first and second fastening members 13, 14 are described herein to include the hook elements and the loop elements, respectively, the invention is not limited to such fastening means and the other type of fastening means such as pressure-sensitive tape strips may be used so far as the front and rear waist regions 8, 9 can be detachably coupled to each other. It is also possible to combine the first fastening member 13 including the loop elements with the second fastening member 14 including the hook elements. While the construction is described such that the first fastening member 13 is attached directly to the outer sheet 7 and the second fastening member 14 is attached directly to the inner sheet 6, it is also possible to prepare separate retaining sheets for these fastening members and to attach these retaining sheets to the inner sheet 6 or the outer sheet 7.

In the step of interposing the elastic members 15 under tension between the second fastening members 14 and the inner sheet 6, the elastic members 15 may be attached together with the second fastening members 14 to the inner sheet at the same time or the elastic members 15 may be attached to the second fastening members 14 followed by attaching this assembly to the inner sheet 6 so far as a contractile force of the elastic members 15 can be effectively exerted on the second fastening members 14.

Second Embodiment

Figure 6:
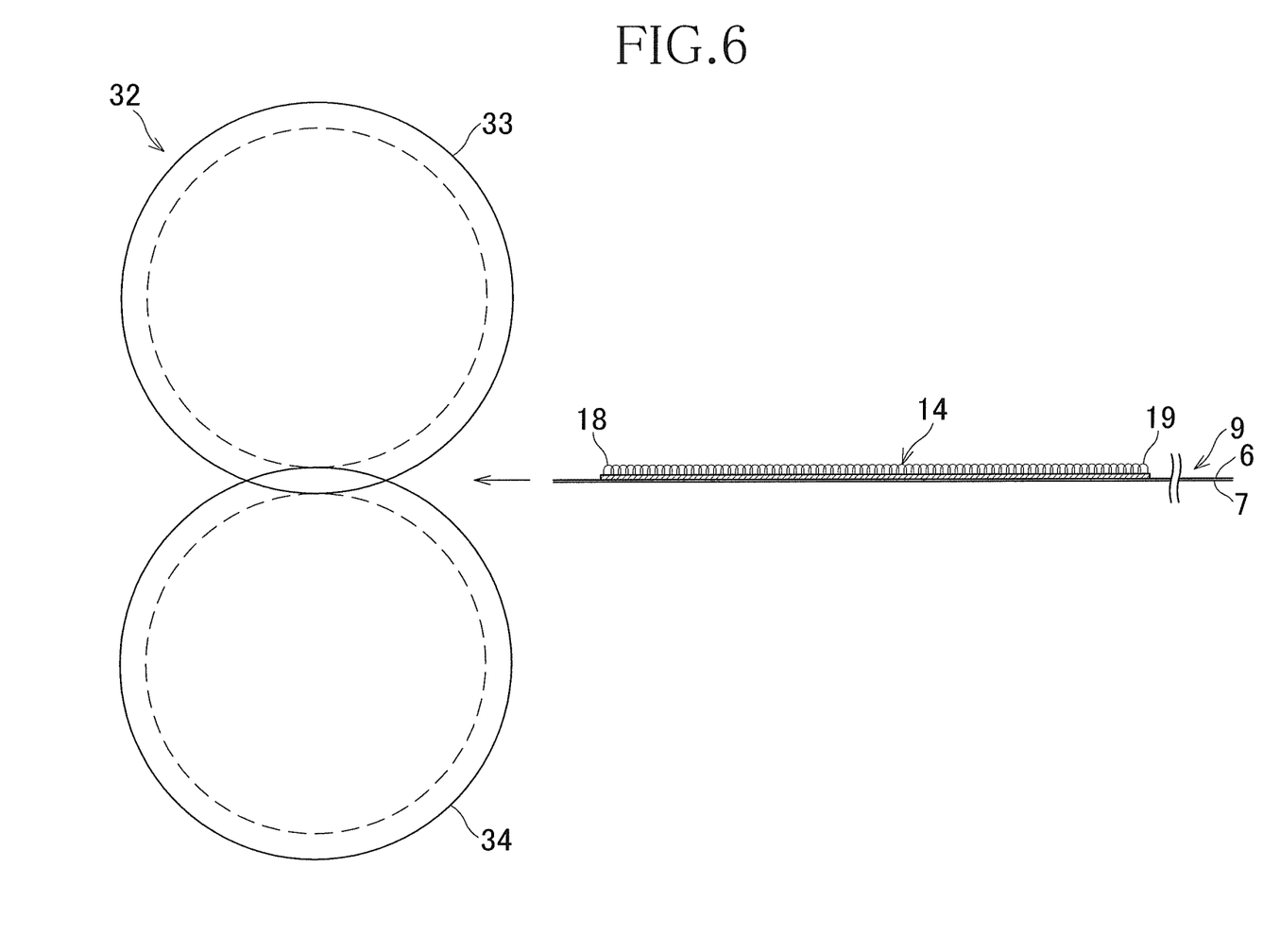
FIG. 6 is a diagram schematically illustrating a second embodiment according to the first aspect of the present invention.
Figure 7:
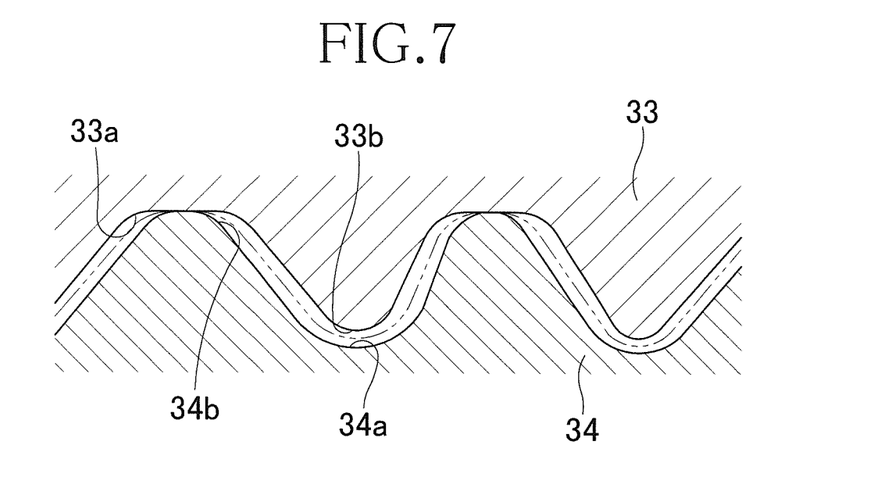
FIG. 7 is a scale-enlarged partial diagram illustrating a gear mechanism.
Figure 8:
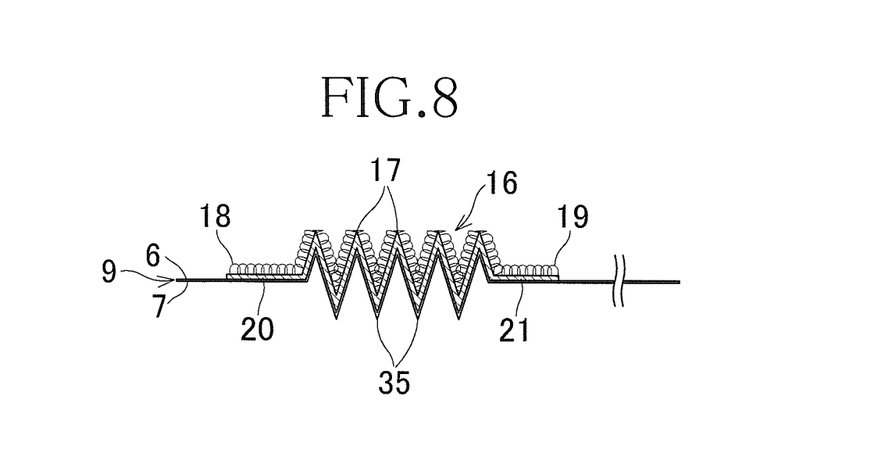
FIG. 8 is a scale-enlarged partial diagram illustrating the second embodiment according to the present invention.

FIG. 6 through 8 illustrate a second embodiment according the present invention. This second embodiment is distinguished from the first embodiment with respect to a method for forming the uneven structure of the second fastening members 14. The other features are similar to those of the first embodiment and description of these similar features will be eliminated.

According to this second embodiment, the uneven structure in the second fastening members 14 is formed by heat deformation occurring in a gear mechanism 32. This means that at least the second fastening members 14 should be made of a thermoplastic resin.

Referring to FIG. 6, the second fastening member 14 is guided to pass through between a first gear 33 and a second gear 34 constituting the gear mechanism 32 to form the uneven structure on the second fastening member 14. In this step, the second fastening member 14 previously attached to the inner sheet 6 along the side edges 12 of the rear waist region 9 is fed together with the inner and outer sheets 6, 7 to the gear mechanism 32. The first gear 33 is heated at a temperature of about 140° C. and the assembly including the second fastening member 14 is fed to the gear mechanism 32 so that the loop elements of the second fastening member 14 may come in contact with the first gear 33. A temperature of the second gear 34 is set to about 20° C.

A manner in which the first gear 33 is engaged with the second gear 34 will be described with reference to FIG. 7. Each trough 33a of the first gear 33 engages with each crest 34b of the second gear 34 with a relatively small clearance left therebetween so that the second fastening member 14 fed together with the inner and outer sheets 6, 7 may come in contact with both the trough 33a and the crest 34b. Each crest 33b of the first gear 33 engages with each trough 34a of the second gear 34 with a clearance left therebetween larger than the clearance left between the trough 33a and the crest 34b so that the first tear 33 or the second gear 34 may be free from contact with the second fastening member 14 fed together with the inner and outer sheets 6, 7.

The assembly composed of the second fastening member 14 and the inner and outer sheets 6, 7 is formed with the uneven structure corresponding to the gear's shape as the second fastening member 14 is fed together with the inner and outer sheets 6, 7 to the gear mechanism 32 and heated in this gear mechanism 32. Specifically, a plurality of the crests 17 of the uneven structure is formed by engagement between the troughs 33a of the first gear 33 and the crests 34b of the second gear 34. Simultaneously, the loop elements of the second fastening member 14 are pressed by the crests 34b against the associated troughs 33a and thereby thermally pressed. In consequence, the loop elements are fused until these loop elements get out of the initial shape and become impossible to be engaged with the hook elements of the first fastening member 13. In other words, no loop is present along the crests of the uneven structure.

The procedure to put the second fastening member 14 in engagement with the first fastening member 13 is substantially similar to the procedure in the first embodiment. The second embodiment is distinguished from the first embodiment in that, even if the uneven region 16 of the second fastening member 14 comes in contact with the first fastening member 13 in the course of positioning by putting the upper end 18, i.e., the flat region 20 of the second fastening member 14 in engagement with the upper end 30 of the first fastening member 13, the second fastening member 14 should not be unintentionally put in engagement with the first fastening member 13. This is because it is impossible for the crests of the uneven region 16 to be engaged with the first fastening member 13. After the step of positioning, the flat region 21 defined in the vicinity of the lower end 19 of the second fastening member 14 may be pulled to unfold the uneven structure and put in engagement with the first fastening member 13 to assure a desired confirm engagement between first and second fastening members 13, 14.

According to this embodiment, the uneven region 16 is formed by the gear mechanism 32 and thereby it is ensured that a dimension of the unevenness, more strictly, a dimension from the crest 17 to the trough 35 is constant and the crests 17 as well as the troughs 35 are reliably formed in the transverse direction X. This means that the uneven structure is evenly unfolded as the second fastening member 14 is pulled downward with the flat region 21 held by the fingers and the second fastening member 14 can be engaged, substantially in flat state, with the first fastening member 13 to assure a firm engagement.

When the uneven structure according to this embodiment is in a contracted state, a dimension between each pair of the adjacent crests 17 is about 7 mm and a dimension from the crest 17 to the trough 35 is about 3 mm. It should be noted here that these dimensions may be appropriately selected depending on various characteristics such as stiffness of the second fastening member 14 or the inner and outer sheets 6, 7, and the invention is not limited to the specific values as have been mentioned above.

While the second fastening member 14 is fed together with the inner sheet 6 to which the second fastening member 14 attached to the gear mechanism 32 according to this embodiment, it is also possible to feed the second fastening member 14 alone to the gear mechanism 32 to form the uneven structure followed by attaching the second fastening member 14 to the inner sheet 6.

It is also possible to incorporate the elastic member 15 according to the first embodiment in the second fastening member 14 according to the second embodiment. In this case, the second fastening member 14 alone is fed to the gear mechanism 32 to form the uneven structure which is, in turn, unfolded and attached to the associated side edge of the rear waist region so that the elastic member 15 may attached under tension between the second fastening member 14 and the inner sheet 6 along the associated side edge 12. The presence of the elastic member 15 allows the uneven structure in the uneven region 16 to be maintained even if engagement and disengagement between the first fastening member 13 and the second fastening member 14 is repeated.

The invention claimed is:

1. A wearing article comprising:
    a liquid-absorbent chassis having a longitudinal direction, a transverse direction, an inner side facing the wearer's skin, an outer side facing the wearer's garment, a front waist region, a rear waist region and a crotch region extending between the front and rear waist region;
    fastening means adapted to detachably fasten said front and rear waist regions to each other along respective pairs of side edges thereof opposed in said transverse direction and extending in said longitudinal direction,
    said fastening means comprise strips of first fastening members attached to said side edges of said front waist region so as to extend in said longitudinal direction and second fastening members attached to said side edges of said rear waist region and extending in said longitudinal direction so as to be detachably engaged with said first fastening members,
    said strips of the first and second fastening members are selected from the group consisting of:
        i) strips of pressure-sensitive tapes; and
        ii) a pair of strips including a series of rows of a plurality of hook elements and a series of rows of a plurality of loop elements and adapted to be detachably engageable with said hook elements, said series of rows of a plurality of hook elements being provided on one of said strips of said first and second fastening members and said series of rows of a plurality of loop elements being provided on the other of said strips of said first and second fastening members;
    each of said strips of the first fastening member or second fastening members is provided with elastic members attached under tension in the longitudinal direction; and
    each of said first fastening members or each of said second fastening members is formed with a corrugated region having a corrugated structure including a plurality of crests extending in said transverse direction and spaced apart from one another in said longitudinal direction and being elastically extendible in said longitudinal direction,
    wherein said strips of said first fastening member or said second fastening member provided with said corrugated structure has at least one flat region at upper and/or lower ends opposed to each other in the longitudinal direction, wherein said flat region is formed with none of the crests.

2. The wearing article according to claim 1, wherein said strips of first fastening members or the second fastening members provided with the corrugated structures are made of thermoplastic resin and formed by thermally deforming the strips of first fastening members or the second fastening members.

3. The wearing article according to claim 2, wherein said crests are non-functionalized as a result of thermal deforming process so that said first fastening members and said second fastening members can no more be engaged one with another.

* * * * *